(12) United States Patent
Collis

(10) Patent No.: US 6,433,160 B1
(45) Date of Patent: *Aug. 13, 2002

(54) METHOD FOR PURIFICATION AND MANIPULATION OF NUCLEIC ACIDS USING PARAMAGNETIC PARTICLES

(75) Inventor: Matthew P. Collis, Seven Valleys, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/417,199

(22) Filed: Oct. 8, 1999

Related U.S. Application Data

(62) Division of application No. 09/183,127, filed on Oct. 30, 1998, now Pat. No. 5,973,138.

(51) Int. Cl.[7] .................. C07H 21/00; C12Q 1/68; C12P 19/34
(52) U.S. Cl. ............... 536/25.4; 536/25.41; 435/6; 435/91.1
(58) Field of Search ............... 536/25.41, 25.4; 435/6, 91.1

(56) References Cited

U.S. PATENT DOCUMENTS

| | | |
|---|---|---|
| 280,130 A | 6/1883 | Camp |
| 3,970,518 A | 7/1976 | Giaever .............. 195/1.5 |
| 3,985,649 A | 10/1976 | Eddelman ............. 210/42 |
| 4,018,886 A | 4/1977 | Giaever .............. 424/12 |
| 4,141,687 A | 2/1979 | Forrest et al. ......... 23/230 R |
| 4,230,685 A | 10/1980 | Senyei et al. .......... 424/12 |
| 4,272,510 A | 6/1981 | Smith et al. .......... 427/47 |
| 4,438,068 A | 3/1984 | Forrest ............... 422/61 |
| 4,672,040 A | 6/1987 | Josephson ............ 436/526 |
| 4,695,393 A | 9/1987 | Whitehead et al. ..... 252/62.54 |
| 4,774,265 A | 9/1988 | Ugelstad et al. ....... 521/55 |
| 4,793,973 A | 12/1988 | Ringrose ............. 422/102 |
| 4,900,677 A | 2/1990 | Hewitt .............. 435/259 |
| 4,923,978 A | 5/1990 | McCormick ........... 536/27 |
| 4,935,342 A | 6/1990 | Seligson et al. ....... 435/6 |
| 4,946,952 A | 8/1990 | Kiefer ............... 536/27 |
| 5,075,430 A | 12/1991 | Little ................ 536/27 |
| 5,129,936 A * | 7/1992 | Wilson .............. 423/558 |
| 5,232,782 A | 8/1993 | Charmot ............. 428/405 |
| 5,234,809 A | 8/1993 | Boom et al. .......... 435/91 |
| 5,395,688 A | 3/1995 | Wang et al. .......... 428/327 |
| 5,458,785 A | 10/1995 | Howe et al. .......... 210/695 |
| 5,491,068 A | 2/1996 | Benjamin et al. ...... 435/7.32 |
| 5,512,439 A | 4/1996 | Hornes et al. ........ 435/6 |
| 5,536,644 A | 7/1996 | Ullman et al. ........ 435/7.25 |
| 5,602,042 A | 2/1997 | Farber .............. 436/526 |
| 5,647,994 A | 7/1997 | Tuunanen et al. ..... 210/695 |
| 5,695,946 A | 12/1997 | Benjamin et al. ..... 435/7.32 |
| 5,705,628 A | 1/1998 | Hawkins ............ 536/25.4 |
| 5,916,539 A * | 6/1999 | Pilgrimm ........... 424/646 |
| 5,925,573 A | 7/1999 | Colin et al. ......... 436/525 |
| 5,928,958 A | 7/1999 | Pilgrimm ........... 436/526 |
| 5,973,138 A * | 10/1999 | Collis .............. 435/6 |
| 6,090,935 A | 7/2000 | Breivik et al. ....... 536/25.4 |

FOREIGN PATENT DOCUMENTS

| | | | |
|---|---|---|---|
| EP | 0 209 490 | 1/1987 | |
| EP | 0 265 244 B1 | 10/1987 | ......... G01N/33/543 |
| EP | 0 444 120 B1 | 11/1989 | ............ C12Q/1/68 |
| EP | 0 446 260 B1 | 11/1989 | ............ C12Q/1/68 |
| EP | 0 818 461 A2 | 1/1998 | |
| WO | WO 96/09379 | 3/1996 | |
| WO | WO 96/18731 | 6/1996 | |
| WO | WO 98/31840 | 7/1998 | |

* cited by examiner

*Primary Examiner*—Johann Richter
*Assistant Examiner*—Howard V. Owens
(74) *Attorney, Agent, or Firm*—David W. Highet

(57) ABSTRACT

The present invention relates to a composition which is useful for the reversible binding of a nucleic acid molecule. The composition, which may be packaged in a kit, includes a paramagnetic particle in an acidic solution.

3 Claims, No Drawings

METHOD FOR PURIFICATION AND MANIPULATION OF NUCLEIC ACIDS USING PARAMAGNETIC PARTICLES

This application is a division of Ser. No. 09/183,127 issued Oct. 30, 1998 now U.S. Pat. No. 5,973,138.

BACKGROUND OF THE INVENTION

Access to cellular components such as nucleic acids is imperative to a variety of molecular biology methodologies. Such methodologies include nucleic acid sequencing, direct detection of particular nucleic acid sequences by nucleic acid hybridization and nucleic acid sequence amplification techniques.

The preparation and purification of high-purity double-stranded (ds) plasmid DNA, single-stranded (ss) phage DNA, chromosomal DNA, agarose gel-purified DNA fragments and RNA is of critical importance in molecular biology. Ideally, a method for purifying nucleic acids should be simple, rapid and require little. if any, additional sample manipulation. Nucleic acids rendered by such a method should be immediately amenable to transformation, restriction analysis, litigation or sequencing. A method with all of these features would be extremely attractive in the automation of nucleic acid sample preparation, a goal of research and diagnostic laboratories.

Typically, the preparation of plasmid DNA from crude alcohol precipitates is laborious, most often utilizing CsCl gradients, gel filtration, ion exchange chromatography, or RNase, proteinase K and repeated alcohol precipitation steps. These methods also require considerable downstream sample preparation to remove CsCl and other salts, ethidium bromide and alcohol. Similar arguments extend when using any of these methods for purifying DNA fragments. A further problem with these methods is that small, negatively-charged cellular components can co-purify with the DNA. Thus, the DNA can have an undesirable level of contamination.

Nucleic acids can also be purified using solid phases. Conventional solid phase extraction techniques have utilized surfaces which either (1) fail to attract and hold sufficient quantities of nucleic acid molecules because of surface design to permit easy recovery of the nucleic acid molecules during elution, or (2) excessively adhere nucleic acid molecules to the surface, thereby hindering recovery of the nucleic acid molecules during elution. Conventional metal surfaces which cause these problems when utilized in solid phase extraction include certain silica surfaces such as glass and Celite. Adequate binding of nucleic acids to these types of surfaces can be achieved only by utilizing high concentrations of chaotropes or alcohols which are generally toxic, caustic, and/or expensive. For example, it is known that DNA will bind to crushed glass powders and to glass fiber filters in the presence of chaotropes. The chaotropic ions typically are washed away with alcohol, and the DNAs are eluted with low-salt solutions or water. Importantly, RNA and protein do not bind. However, a serious drawback in the use of crushed glass powder is that its binding capacity is low. In addition. glass powders often suffer from inconsistent recovery, incompatibility with borate buffers and a tendency to nick large DNAs. Similarly, glass fiber filters provide a nonporous surface with low DNA binding capacity. Other silicas, such as silica gel and glass beads, are not suitable for DNA binding and recovery. Currently, the solid phase of choice for solid phase extraction of DNA is Celite such as found in Prep-A-Gene™ by Bio-Rad Laboratories.

As with the crushed glass powders, high concentrations of chaotropes are required for adequate binding of the DNA to the Celite.

However, the hydration of silica substances has, in some instances resulted in elimination of the need for such high concentrations of chaotropes to elute bound DNA from the silica substance as taught in references such as EP 0 512 767, EP 0 585 660, U.S. Pat. No. 5,674,997 and EP 0 832 897.

There are numerous protocols for purifying DNA. For example, U.S. Pat. No. 4,923,978 discloses a process for purifying DNA in which a solution of protein and DNA is passed over a hydroxylated support and the protein is bound and the DNA is eluted. U.S. Pat. No. 4,935,342 discloses purification of DNA by selective binding of DNA to anion exchangers and subsequent elution. U.S. Pat. No. 4,946,952 discloses DNA isolation by precipitation with water-soluble ketones. A DNA purification procedure using chaotropes and dialyzed DNA is disclosed in U.S. Pat. No. 4,900,677.

Diatoms have also been utilized for purification of nucleic acids as evidenced by U.S. Pat. No. 5,234,809 to Boom et al. and U.S. Pat. No. 5,075,430 to Little et al.

Yet a further technique utilized for purification of nucleic acids is binding to specifically adapted paramagnetic particles. Examples of such techniques may be found in references such as European Specification EP 0 446 260 B1 and U.S. Pat. No. 5,512,439 (Homes et al.) which describe monodisperse, superparamagnetic particles having a particle diameter standard deviation of less than 5%. Each particle carries a plurality of molecules of an oligonucleotide, with each oligonucleotide having a section serving as a probe for a target nucleic acid molecule of interest.

U.S. Pat. No. 4,672,040 (Josephson) and U.S. Pat. No. 4,695,393 (Whitehead et al.) describe magnetically responsive particles for use in systems to separate certain molecules. The particles have a metal oxide core surrounded by a stable silicone coating to which organic and/or biological molecules may be coupled.

U.S. Pat. No. 3,970,518 (Giaever) describes a method of sorting and separating a select cell population from a mixed cell population. The method utilizes small magnetic particles which are coated with an antibody to the select cell populations.

U.S. Pat. No. 4,141,687 (Forrest et al.) describes an automatic apparatus and method to assay fluid samples. The apparatus utilizes a particulate material with a reagent bound thereto. The particulate material is magnetic, and the reagent is a substance which takes part in a reaction in the reaction mixture.

U.S. Pat. No. 4,230,685 (Senyei et al.) describes a method for magnetic separation of cells. The method utilizes magnetically-responsive microspheres which are coated with staphylococcal Protein A to which is bound antibody.

U.S. Pat. No. 4,774,265 (Ugelstad et al.) describes a process for preparing magnetic polymer particles. The particles are compact or porous polymer particles treated with a solution of iron salts.

U.S. Pat. No. 5,232,782 (Charmot) describes magnetizable "core-shell" microspheres which have a core of a magnetizable filler and a shell of crosslinked organopolysiloxane.

U.S. Pat. No. 5,395,688 (Wang et al.) describes magnetically responsive fluorescent polymer particles which have a polymeric core coated evenly with a layer of polymer containing magnetically responsive metal oxide.

U.S. Pat. No. 5,491,068 and U.S. Pat. No. 5,695,946 (Benjamin et al.) describe an assay method for detecting the presence of bacteria using magnetic beads with specific antibodies immobilized thereon.

U.S. Pat. No. 5,536,644 (Ullman et al.) describes a particle separation method. The method utilizes magnetic particles with surface functional groups, and optionally, an additional surface coating.

European Patent Specification EP 0 444 120 B1 (Homes et al.) describes a method for detection of target RNA or DNA. The method utilizes magnetic particles carrying a single stranded 5'-attached DNA probe capable of binding the target RNA or DNA.

International Publication No. WO 96/18731 (Deggerdal et al.) describes a method for isolating nucleic acid from a sample using a particulate solid support and an anionic detergent.

U.S. patent No. 5,705,628 (Hawkins) describes a method for DNA purification and isolation using magnetic particles with functional group-coated surfaces.

SUMMARY OF THE INVENTION

In order to provide a more effective and efficient technique for the purification and manipulation of nucleic acids, the present invention relates to a composition useful for reversible binding of a nucleic acid molecule. The composition includes a paramagnetic particle in an acidic environment. The invention also includes such a composition packaged as a kit, as well as methods utilizing such a composition to reversibly bind a nucleic acid molecule.

DETAILED DESCRIPTION OF THE INVENTION

The present invention relates to unique compositions of matter. More specifically, the composition of matter is a paramagnetic particle in an acidic solution, that is, a solution having a pH of less than about 7.0.

The Applicants found that when in an acidic environment, paramagnetic particles will reversibly bind nucleic acid molecules without the necessity of an anionic detergent as taught in International Publication No. WO 96/18731. Although not desiring to be bound by a particular theory, the Applicants believe that an acidic environment increases the electropositive nature of the iron portion of the molecules, and thus increases the binding of the molecules to the electronegative phosphate portion of a nucleic acid molecule.

As used herein, the term paramagnetic particles means particles which are capable of having a magnetic moment imparted to them when placed in a magnetic field. Therefore, such paramagnetic particles, when in such a magnetic field, are movable under the action of such a field. Such movement is useful for moving bound nucleic acid molecules for different aspects of a sample processing protocol or other manipulations. Thus, nucleic acid molecules bound to the paramagnetic particles can be moved to different areas for exposure to different reagents and/or conditions with minimal direct contact due to the application of magnetic force.

The Applicants have found that paramagnetic particles useful in the present invention need not be complicated structures. Thus, iron particles are useful in the present invention, and the iron may be an iron oxide of forms such as ferric hydroxide and ferrosoferric oxide, which have low solubility in an aqueous environment. Other iron particles such as iron sulfide and iron chloride may also be suitable for binding and extracting nucleic acids using the conditions described herein.

Similarly, the shape of the paramagnetic particles is not critical to the present invention. Thus, the paramagnetic particles may be of various shapes, including for example, spheres, cubes. oval, capsule-shaped, tablet-shaped, nondescript random shapes, etc., and may be of uniform shape or non-uniform shapes. Whatever the shape of a paramagnetic particle, its diameter at its widest point is generally in the range of from about 0.5 $\mu$m to about 20 $\mu$m.

The acidic environment in which the paramagnetic particles effectively, reversibly bind nucleic acid molecules can be provided through a variety of means. For example, the paramagnetic particles can be added to an acidic solution, or an acidic solution may be added to the particles. Alternatively a solution or environment in which the paramagnetic particles are located can be acidified by addition of an acidifying agent such as hydrochloric acid, sulfuric acid, acetic acid and citric acid.

Provided that the environment in which the paramagnetic particles are located is of a pH less than about 7.0, the particles will reversibly bind nucleic acid molecules. Furthermore, the Applicants have found that the nucleic acid binding capacity of the paramagnetic particles increases as the pH decreases.

The acidic environment for the paramagnetic particles of the present invention is believed to allow for elimination of the need for detergents as taught in certain references such as International Publication No. WO 96/18731. Without desiring to be held to a particular theory, the Applicant believes that detergents are not necessary for the present invention, because the acidic solution of the present invention promotes the binding of electropositive paramagnetic particles to electronegative nucleic acid molecules in preference to other substances in a sample such as nucleic acid hybridization and amplification inhibitors. In contrast, the utilization of detergents as taught in references such as International Publication No. WO 96/18731 is solubilize nucleic acid hybridization and amplification inhibitors in order that such inhibitors do not interfere with binding of nucleic acid molecules to paramagnetic particles.

As stated above, in an acidic environment, electropositive paramagnetic particles, such as ferric oxide particles, will bind electronegative nucleic acid molecules. Thus, other materials in the environment, such as inhibitors of nucleic acid hybridization and amplification can be separated from the bound nucleic acid molecules. Such separation can be accomplished by means known to those skilled in the art, such as centrifugation, filtering or application of magnetic force.

The bound nucleic acid molecules can then be eluted into an appropriate buffer for further manipulation, such as hybridization or amplification reactions. Such elution can be accomplished by heating the environment of the particles with bound nucleic acids and/or raising the pH of such environment. Agents which can be used to aid the elution of nucleic acid from paramagnetic particles include basic solutions such as potassium hydroxide, sodium hydroxide or any compound which will increase the pH of the environment to an extent sufficient that electronegative nucleic acid is displaced from the particles.

The following examples illustrate specific embodiments of the invention described in this document. As would be apparent to skilled artisans, various changes and modifications are possible and are contemplated within the scope of the invention described.

EXAMPLE 1

Nucleic Acid Binding with Iron Oxide

This example was designed to compare binding of nucleic acid with iron oxide to binding of nucleic acid with zirconium at three target input levels.

The following materials were used in this example.

A *Chlamydia trachomatis* preparation

Phosphate buffer

Sample buffer for the BDProbeTec™ ET system

Hydrated Iron Oxide FeO(OH) particles (30 mesh=300–1200 microns)

Hydrated Zirconium Oxide

Glycine HCl

*Chlamydia trachomatis* Priming and Amplification Wells for the BDProbeTec™ ET system Ethyl Alcohol The procedure followed for the example was as follows.

*Chlamydia trachomatis* solutions at 5,000 Elementary Bodies(EB)/ml, 1,000 EB/ml, 500 EB/ml and 0 EB/ml were prepared in phosphate buffer and each solution was transferred to twelve 2.0 ml centrifuge tubes/spike level. The tubes were heated at 105° C. for 30 minutes. Hydrated iron oxide particles washed with $DiH_2O$ by gravity were dispensed into six tubes at each of the *Chlamydia trachomatis* spike levels at 10 mg/tube. Hydrated zirconium particles were dispensed into three tubes containing each *Chlamydia trachomatis* spike level at 10 mg/tube. No particles were added to three tubes of each level. Thirty ul of 3M Glycine-HCl was dispensed into each tube described above, and the tubes were placed on a end over end rocker for 30 minutes. Three tubes/spike level of the iron oxide tubes, the hydrated zirconium tubes and the tubes containing no particles were centrifuged to separate, and were washed once with one ml/tube of 95% ETOH, once with one ml/tube of $DiH_2O$ and were re-suspended with one ml/tube of sample buffer. The other three tubes/spike level containing iron oxide were magnetically separated by placing a magnet adjacent the tube, the samples extracted, and the tubes were washed with 1.0 ml of ETOH/tube. The solution was magnetically separated for 3.0 minutes and 1.0 ml of sample buffer was added to each tube. The tubes were heated for 30 minutes at 105° C. and were amplified in the *Chlamydia trachomatis* BDProbeTec™ ET system. The BDProbeTec™ ET system is. a publicly disclosed, semi-automated system for the homogeneous amplification and real time detection of nucleic acid target molecules.

The results of this example were as follows.

| PARTICLE TYPE | CHLAMYDIA LEVEL | MEAN MOTA VALUES |
| --- | --- | --- |
| Hydrated Zirconium | 0 | 195 |
| Hydrated Zirconium | 500 | 3813 |
| Hydrated Zirconium | 1,000 | 30843 |
| Hydrated Zirconium | 5,000 | 23872 |
| NONE | 0 | 181 |
| NONE | 500 | 107 |
| NONE | 1,000 | 220 |
| NONE | 5,000 | 333 |
| Hydrated Iron Oxide, centrifuge wash | 0 | 162 |
| Hydrated Iron Oxide, centrifuge wash | 500 | 7421 |
| Hydrated Iron Oxide, centrifuge wash | 1,000 | 6552 |
| Hydrated Iron Oxide, centrifuge wash | 5,000 | 24415 |
| Hydrated Iron Oxide, magnetic wash | 0 | 203 |
| Hydrated Iron Oxide, magnetic wash | 500 | 8956 |
| Hydrated Iron Oxide, magnetic wash | 1,000 | 5243 |
| Hydrated Iron Oxide, magnetic wash | 5,000 | 20294 |

The conclusions drawn from the results were as follows.

The MOTA values (sum of individual measurement units over time) are an internal Becton Dickinson fluorescent unit with an established cutoff level for positivity at 1,000 MOTA. Magnetically separated iron oxide produced the same positivity as the hydrated zirconium particles. The tubes containing no particles produced no carry over results even at the 5,000 EB/ml level. This experiment demonstrated that hydrated iron oxide binds DNA under acidic conditions.

EXAMPLE 2

Elution and Denaturation of Double Stranded DNA from Iron Oxide Particles

Using Potassium Hydroxide

This example was performed to determine whether DNA could be eluted and denatured using potassium hydroxide (KOH) alone without heat. In addition, the example was performed to determine which neutralization/sample buffer produces optimum MOTA values.

The materials used in this example were as follows.

a 70 mM KOH solution a 100 mM Bicine, 2× *Chlamydia trachomatis* sample buffer (20% DMSO, 18% Glycerol, 0.06% Proclin, 0.013 mM Tween 20 and 60 mM $KPO_4$)

a 200 mM Bicine, 2× *Chlamydia trachomatis* sample buffer a 300 mM Bicine, 2× *Chlamydia trachomatis* sample buffer a *Chlamydia trachomatis* sample buffer (10% DMSO, 9% Glycerol, 0.03% Proclin, 0.0065 mM Tween 20 and 30 mM $KPO_4$)

Hydrated zirconium particles

Hydrated iron oxide particles a *Chlamydia trachomatis* preparation

95% Ethyl alcohol (ETOH)

Phosphate buffer

The procedure followed for this example was as follows.

*Chlamydia trachomatis* solutions were prepared at 1,000 EB/ml and 5,000 EB/ml in phosphate buffer and were dispensed into 32 two ml centrifuge tubes/spike level at 1.0 ml/tube. Hydrated iron oxide was dispensed into 16 tubes/spike level at 10 mg/tube and 60 ul of 3M glycine HCl was added to each tube. Hydrated zirconium particles were dispensed into 16 tubes/spike level at 10 mg/tube and 30 ul of 3M glycine HCl was added to each tube. The tubes were maintained on an end over end rotator for 30 minutes. The iron oxide tubes were magnetically separated, and then washed with 1.0 ml of ETOH and then 1.0 ml of $DiH_2O$. The zirconium particle tubes were centrifuge washed once with one ml of ETOH and then with one ml of $DiH_2O$. Twelve tubes of each particle type and spike level had 500 ul of 70 mM KOH added to each tube for 15 minutes. Of the twelve tubes, four tubes of both particle type and spike level had 100 mM 2× *Chlamydia trachomatis* sample buffer (w/phosphate) added to each tube at 500 ul. Of the twelve tubes, four tubes of both particle types and spike levels had 200 mM 2× *Chlamydia trachomatis* sample buffer (w/phosphate) added to each tube at 500 ul. Of the twelve tubes, four tubes of both particle types and spike levels had 300 mM 2× *Chlamydia trachomatis* sample buffer (w/phosphate) added to each tube at 500 ul. To the four remaining tubes, 1.0 ml of sample buffer was added. Two tubes of each particle type, spike level and buffer type were placed in a boiling water bath for five minutes. The sample fluid was then immediately amplified in the *Chlamydia trachomatis* BDProbeTec™ ET system.

The results of this example were as follows.

| Bicine Concentration | Chlamydia Concentration | Iron Oxide No Heat | Iron Oxide Heat | Zirconium No Heat | Zirconium Heat |
|---|---|---|---|---|---|
| 100 mM | 1,000 EB/ml | 214 | 298 | 1032 | 11556 |
| 200 mM | 1,000 EB/ml | 3106 | 123 | 1320 | 7250 |
| 300 mM | 1,000 EB/ml | 1318 | 4871 | 113 | 5833 |
| Control | 1,000 EB/ml | 280 | 4775 | 3245 | 7988 |
| 100 mM | 5,000 EB/ml | 814 | 3711 | 24565 | 38873 |
| 200 mM | 5,000 EB/ml | 5495 | 19173 | 11415 | 32871 |
| 300 mM | 5,000 EB/ml | 13433 | 15302 | 18298 | 18127 |
| Control | 5,000 EB/ml | 422 | 17106 | 4753 | 20208 |

The conclusions drawn from the results above were as follows.

The results indicate that DNA can be eluted and denatured from hydrated iron oxide and hydrated zirconium oxide particles with KOH alone (w/o heat) and that the neutralization buffers which produced optimum MOTA values were the 200 and 300 mM Bicine 2× neutralization buffers.

EXAMPLE 3

Extraction of Nucleic Acid From Urine Samples Using Hydrated Iron Oxide

This example was performed to determine if hydrated iron oxide at low pH can be used to extract *Chlamydia trachomatis* DNA from spiked urine samples.

The materials used in this example were as follows.
Urine samples
*Chlamydia trachomatis* preparations
Sample buffer
Hydrated zirconium particles
Hydrated iron oxide particles
95% Ethyl Alcohol (ETOH)
Glycine HCl
BDProbeTec™ ET system *Chlamydia trachomatis* primer wells and amplification wells The procedure followed for this example was as follows.
Each of ten urine samples were split into three two ml aliquots and the urine samples were spiked with *Chlamydia trachomatis* preparation at 1,000 EB/ml, 2,500 EB/ml and 5,000 EB/ml. The urine samples were split into 1.0 ml volumes in two ml centrifuge tubes. Then, 10 mg of hydrated iron oxide particles were dispensed into one tube at each spike level for each sample. Sixty ul of 3M Glycine HCl was added to each iron oxide tube. The tubes were maintained on an end over end rotator for 30 minutes. In addition, 10 mg of hydrated zirconium particles were dispensed into one tube at each spike level for each sample. Thirty ul of 3 M Glycine HCl was added to each tube containing hydrated zirconium. The tubes were maintained on an end over end rotator for 30 minutes. The tubes containing hydrated zirconium particles were centrifuge washed at 10,000 g using one ml of ETOH and then one ml of DiH$_2$O. The tubes were re-suspended with 1.0 ml of sample buffer. The tubes containing iron oxide particles were magnetically separated, and then washed using one ml of ETOH and then 1.0 ml of DiH$_2$O and the tubes were re-suspended with 1.0 ml of sample buffer. The sample fluid from each tube was boiled for 5 minutes and then amplified using the *Chlamydia trachomatis* BDProbeTec™ ET system.

The results of this example were as follows.

| Chlamydia Level | Particle Type | Positives |
|---|---|---|
| 1,000 EB/ml | Hydrated Iron Oxide | 3/10 |
| 1,000 EB/ml | Hydrated Zirconium | 9/10 |
| 2,500 EB/ml | Hydrated Iron Oxide | 10/10 |
| 2,500 EB/ml | Hydrated Zirconium | 10/10 |
| 5,000 EB/ml | Hydrated Iron Oxide | 10/10 |
| 5,000 EB/ml | Hydrated Zirconium | 10/10 |

The conclusions drawn from the above results were as follows.

The detectable positivity rate drops at the same level with either the hydrated zirconium particles or the hydrated iron oxide particles. This indicates similar performance with both particles types. Iron oxide at low pH can extract DNA from urine samples.

EXAMPLE 4

Extraction of Nucleic Acid From Plasma Samples Using Hydrated Iron Oxide

This example was performed to determine if hydrated iron oxide at low pH can be used to extract *Chlamydia trachomatis* DNA from spiked plasma samples. In addition, this example was performed to compare a plasma DNA extraction method using hydrated zirconium particles to a plasma DNA extraction method using hydrated iron oxide particles.

The materials used for this example were as follows.
300 mM Bicine 2× *Chlamydia trachomatis* sample buffer
Hydrated iron oxide particles
Hydrated zironium oxide particles
Guanidine isothiocynate
*Chlamydia trachomatis* stock preparation
*Chlamydia trachomatis* BDProbeTec™ ET primer wells and amplification wells
Internal Amplification Control (IAC) BDProbeTec™ ET primer wells and amplification wells
150 mM KOH
Plasma samples
95% Ethyl alcohol The procedures followed for this example was as follows.

Iron Oxide Procedure

One ml of DiH$_2$O was added to eight two ml centrifuge tubes containing 40 mg of hydrated iron oxide particles. Two plasma samples were spiked with *Chlamydia trachomatis* preparation at 9,000 EB/300 ul, 6,000 EB/300 ul, 3,000 EB/300 ul and 1,500 EB/300 ul. Then, 300 ul of each spiked plasma sample was added to the tubes containing hydrated iron oxide particles. The tubes were heated at 105° C. for 30 minutes. Eighty ul of glacial acetic acid was then added to each tube, and the tubes were placed on an end over end rotator for 30 minutes. The tubes were then placed on a magnetic tube rack and the treated sample. fluid was removed. The tubes were magnetically separated, and then washed with 1.0 ml of 25 mM acetic acid twice. The DNA was eluted from the hydrated iron oxide particles with 500 ul of 150 mM KOH for 15 minutes. The solutions were neutralized with 500 ul of 300 mM 2× sample buffer. The samples were placed in a boiling water bath for five minutes. The samples were then amplified using the BDProbeTec™ ET *Chlamydia trachomatis* system.

Hydrated Zirconium Procedure

The same two plasma samples from the iron oxide procedure above were dispensed at 300 ul/tube into four 2.0 ml centrifuge tubes for each plasma sample. Five molar guanidine isothiocynate (GITC) was added to each tube at 700 ul. The four tubes of each sample were spiked with *Chlamydia trachomatis* preparation at 9,000 EB/300 ul, 6,000 EB/300 ul, 3,000 EB/300 ul and 1,500 EB/300 ul, respectively, and the tubes were maintained at room temperature for 15 minutes. A hydrated zirconium oxide particle slurry was prepared by combining 10 mg of zirconium oxide particles with 30 ul of 3M glycine HCl. Thirty ul of this slurry was added to each tube and the tubes were placed on an end over end rotator for 30 minutes. The tubes were centrifuged at 10,000 g for 3.0 minutes, the supernatant was removed, and 1.0 ml of 2M GITC was added to each tube. The tubes were centrifuged at 10,000 g for 3.0 minutes, the supernatant was removed and 1.0 ml of 80% ethyl alcohol/20% 50 mM Tris buffer was added to each tube. The tubes were washed two additional times by centrifuging at 10,000 g for 3.0 minutes, extracting the supernatant and adding 1.0 ml of DiH$_2$O. The DNA was eluted in 1.0 ml of 150 mM KOH/300 mM Bicine 2× sample buffer. The samples were placed in a boiling water bath for five minutes. The samples were pop centrifuged at 3,200 g and were amplified using the *Chlamydia trachomatis* BDProbeTec™ ET system.

Internal Amplification Control Procedure

Sample buffer was spiked with *Chlamydia trachomatis* preparation at 9,000 EB/300 ul, 6,000 EB/300 ul, 3,000 EB/300 ul and 1,000 EB/300 ul. The samples were placed in a boiling water bath for five minutes and were amplified using the *Chlamydia trachomatis* BDProbeTec™ ET system.

The results of this example were as follows.

| Particle Type | Spike Level | Chlamydia MOTA Mean | IAC MOTA Mean |
|---|---|---|---|
| Iron oxide | 9,000 | 14871 | 14261 |
| Zirconium | 9,000 | 16774 | 16886 |
| Control | 9,000 | 19808 | 35077 |
| Iron oxide | 6,000 | 8668 | 19313 |
| Zirconium | 6,000 | 19115 | 24339 |
| Control | 6,000 | 22129 | 34234 |
| Iron oxide | 3,000 | 2436 | 16128 |

-continued

| Particle Type | Spike Level | Chlamydia MOTA Mean | IAC MOTA Mean |
|---|---|---|---|
| Zirconium | 3,000 | 20098 | 33188 |
| Control | 3,000 | 21954 | 26355 |
| Iron oxide | 1,000 | 492 | 10021 |
| Zirconium | 1,000 | 15587 | 25805 |
| Control | 1,000 | 2679 | 14423 |

The conclusions drawn from the above results were as follows.

Using a MOTA positivity value of 1,000, hydrated iron oxide was capable of extracting DNA from plasma samples up to 3,000 EB/300 ul.

EXAMPLE 5

Nucleic Acid Capture Using Ferrosoferric oxide (Fe$_3$O$_4$)

This example was designed to compare two nucleic acid capture particles: Ferric Hydroxide (hydrated ferric oxide) and Ferrosoferric oxide under neutral and acidic binding conditions.

The materials used for this example were as follows.

Phosphate buffer

Ferric hydroxide (FeO(OH)) particles

Ferrosoferric oxide (Fe$_3$O$_4$) particles

*Chlamydia trachomatis* preparation

*Chlamydia trachomatis* BDProbeTec™ ET primer wells and amplification wells

Internal Amplification Control (IAC) BDProbeTec™ ET primer wells and amplification wells Acetic acid 150 mM KOH 300 mM Bicine, 2× *Chlamydia trachomatis* sample buffer The procedure followed for this example was as follows.

Ferric hydroxide (FeO(OH)) powder was prepared by mortal and pestle grinding 30–50 mesh material to a fine powder. The powder was allowed to settle in an aqueous solution for four minutes. The supernatant was extracted and the material was allowed to settle for an additional fifteen minutes. The pelleted material was then magnetically separated and was magnetically washed with DiH$_2$O. The material was then filtered onto 20 um filter paper and dried overnight at 37° C. Then, 60 ug of the material was transferred to a tube containing 480 ul of DiH$_2$O. This slurry was dispensed into six 2 ml centrifuge tubes. Also, 240 ug of dried FeO(OH) material was transferred to a tube containing 480 ul of DiH$_2$O. The slurry created was transferred to six 2 ml centrifuge tubes.

In addition, 60 ug of Fe$_3$O$_4$ (sized at 88–92% passing a 325 sieve) was transferred to a tube containing 480 ul of DiH$_2$O. The slurry created was dispensed into six 2 ml centrifuge tubes. Another slurry was created by transferring 240 mg of dried Fe$_3$O$_4$ material to a tube containing 480 ul of DiH$_2$O. This slurry was then transferred to six 2 ml centrifuge tubes. *Chlamydia trachomatis* solutions were prepared at 0 EB/ml, 1,000 EB/ml and 4,000 EB/ml in phosphate buffer. Each concentration of *Chlamydia trachomatis* solution was dispensed into two tubes of each particle type. The tubes were heated at 105° C. for 30 minutes. An 80 ul aliquot of acetic acid was added to one tube of each particle type, and the tubes were maintained on an end over end rocker for 30 minutes. The tubes were then magnetically separated and washed with 1.0 ml of 25 mM acetic acid/wash twice. A 150 mM KOH aliquot was added to each tube at 500 ul/tube for 15 minutes, and 500 ul of 300 mM Bicine 2× sample buffer was added to each tube and the tubes were placed in a boiling water bath for five minutes. The sample fluid was amplified using the *Chlamydia trachomatis* BDProbeTec™ ET system.

The results from this example were as follows.

| Chlamydia Level | Iron Oxide Type | Mass | Acid Volume | Chlamydia MOTA | IAC MOTA |
|---|---|---|---|---|---|
| 0 | FeO(OH) | 10 | 80 | 187 | 10076 |
| 0 | FeO(OH) | 40 | 80 | 127 | 7751 |
| 0 | FeO(OH) | 10 | 0 | 5 | 13928 |
| 0 | FeO(OH) | 40 | 0 | 111 | 13814 |
| 1,000 | FeO(OH) | 10 | 80 | 3343 | 11610 |
| 1,000 | FeO(OH) | 40 | 80 | 11574 | 13886 |
| 1,000 | FeO(OH) | 10 | 0 | 2209 | 11883 |
| 1,000 | FeO(OH) | 40 | 0 | 2350 | 13677 |
| 4,000 | FeO(OH) | 10 | 80 | 5778 | 18752 |
| 4,000 | FeO(OH) | 40 | 80 | 13997 | 10866 |
| 4,000 | FeO(OH) | 10 | 0 | 2195 | 17593 |
| 4,000 | FeO(OH) | 40 | 0 | 4426 | 12065 |
| 0 | $Fe_3O_4$ | 10 | 80 | 34 | 13279 |
| 0 | $Fe_3O_4$ | 40 | 80 | 37 | 11336 |
| 0 | $Fe_3O_4$ | 10 | 0 | 1 | 12965 |
| 0 | $Fe_3O_4$ | 40 | 0 | 2 | 5351 |
| 1,000 | $Fe_3O_4$ | 10 | 80 | 8507 | 17116 |
| 1,000 | $Fe_3O_4$ | 40 | 80 | 3772 | 4923 |
| 1,000 | $Fe_3O_4$ | 10 | 0 | 48 | 15623 |
| 1,000 | $Fe_3O_4$ | 40 | 0 | 7 | 925 |
| 4,000 | $Fe_3O_4$ | 10 | 80 | 7019 | 16337 |
| 4,000 | $Fe_3O_4$ | 40 | 80 | 21486 | 17983 |
| 4,000 | $Fe_3O_4$ | 10 | 0 | 10438 | 17613 |
| 4,000 | $Fe_3O_4$ | 40 | 0 | 206 | 10454 |

The conclusions drawn from the above results were as follows.

Using a MOTA positivity value of 1,000, $Fe_3O_4$ can extract nucleic acid to a level of 1,000 EB/ml, which is comparable to the extraction capability of FeO(OH) with both masses. A negative acid volume negatively impacted both the number of positive values at the lower 1,000 EB/ml level and MOTA values.

While the invention has been described with some specificity, modifications apparent to those with ordinary skill in the art may be made without departing from the scope of the invention. Various features of the invention are set forth in the following claims

What is claimed is:

1. A method for reversibly binding at least one nucleic acid molecule to at least one paramagnetic particle comprising:

(a) providing a suspension of at least one paramagnetic particle in an acidic solution, said acidic solution comprising glycine HCl, and said paramagnetic particle consisting of iron oxide; and (b) combining said suspension with at least one nucleic acid molecule such that said at least one nucleic acid molecule is reversibly bound to said at least one paramagnetic particle.

2. The method of claim 1 wherein the iron oxide is ferrosoferric oxide.

3. The method of claim 2 wherein the acidic solution comprises glycine HCl.

* * * * *